United States Patent [19]
Weissman

[11] Patent Number: 5,100,322
[45] Date of Patent: Mar. 31, 1992

[54] WATER-COOLED FRICTION CONTOUR CUTTING DENTAL TOOL

[76] Inventor: Bernard Weissman, 225 E. 48th St., New York, N.Y. 10017

[21] Appl. No.: 741,286

[22] Filed: Aug. 7, 1991

Related U.S. Application Data

[63] Continuation-in-part of Ser. No. 446,756, Dec. 6, 1989, Pat. No. 5,037,300.

[51] Int. Cl.⁵ .................................................. A61C 3/02
[52] U.S. Cl. ................................... 433/165; 433/166
[58] Field of Search ...................... 433/165, 166, 223

[56] References Cited

U.S. PATENT DOCUMENTS

| | | | |
|---|---|---|---|
| 1,123,730 | 1/1915 | Greenfield | 433/165 |
| 1,333,388 | 3/1920 | Chester | 433/165 |
| 2,250,058 | 7/1941 | Brooks | 433/166 |
| 2,366,767 | 1/1945 | Brooks | 433/166 |
| 2,562,587 | 7/1951 | Swearingen | 433/166 |
| 2,707,329 | 5/1955 | Costoff | 433/166 |
| 2,855,673 | 10/1958 | Gruenwald | 433/166 |
| 3,461,563 | 8/1969 | Nelson | 433/165 |
| 3,979,829 | 9/1976 | Lemos | 433/165 |

FOREIGN PATENT DOCUMENTS 732124 6/1955 United Kingdom ................ 433/165

*Primary Examiner*—John J. Wilson
*Attorney, Agent, or Firm*—Barry G. Magidoff

[57] ABSTRACT

A water-cooled friction-type cutting dental tool is disclosed comprising an at least partially hollow cylindrical body portion having an external circumferential cutting surface, an interior circumferential surface defining a hollow space, and an external annular transverse end cutting surface at one end. The end cutting surface surrounds a central opening to the hollow space; in the hollow space, a centered elongated member is secured so as to be substantially concentric to and held partially within the hollow space and partially extending beyond the hollow space, beyond the end cutting surface. The portion of the elongated member extending beyond the end cutting surface has a smooth rounded surface for limiting the cutting depth of the tool, both longitudinally and transversely. The portion within the hollow space has a cross-sectional dimension such that an annular channel is defined between the elongated member and the interior circumferential surface.

15 Claims, 3 Drawing Sheets

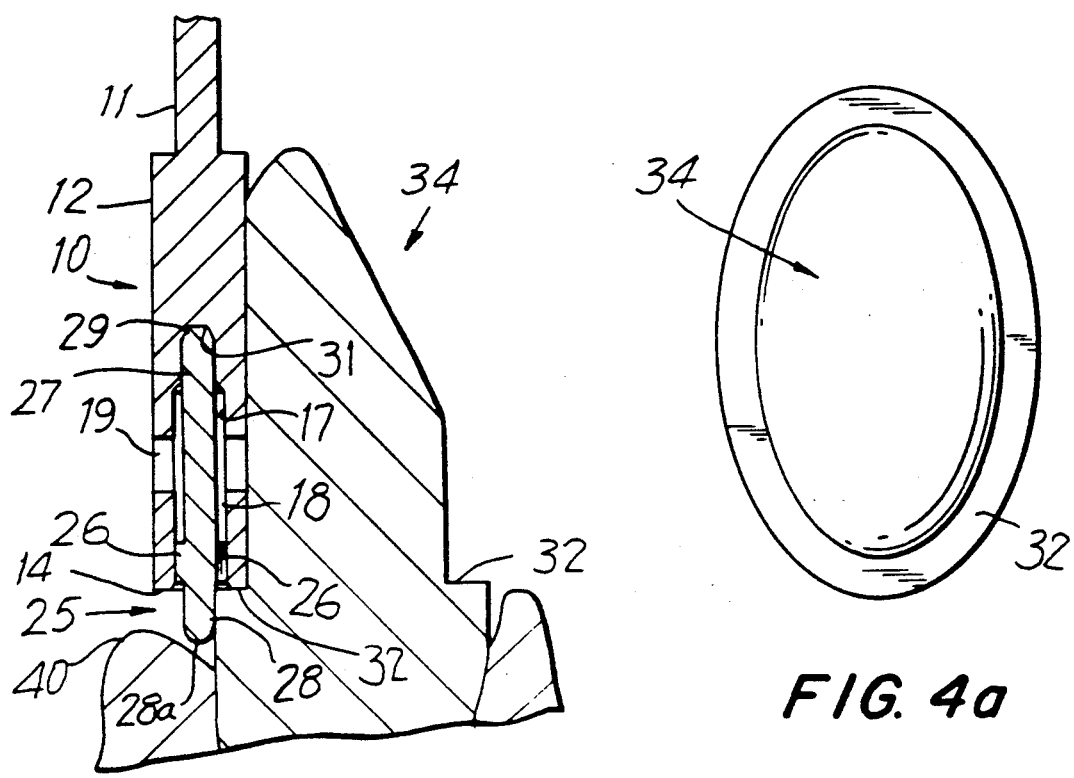
FIG. 4
FIG. 4a
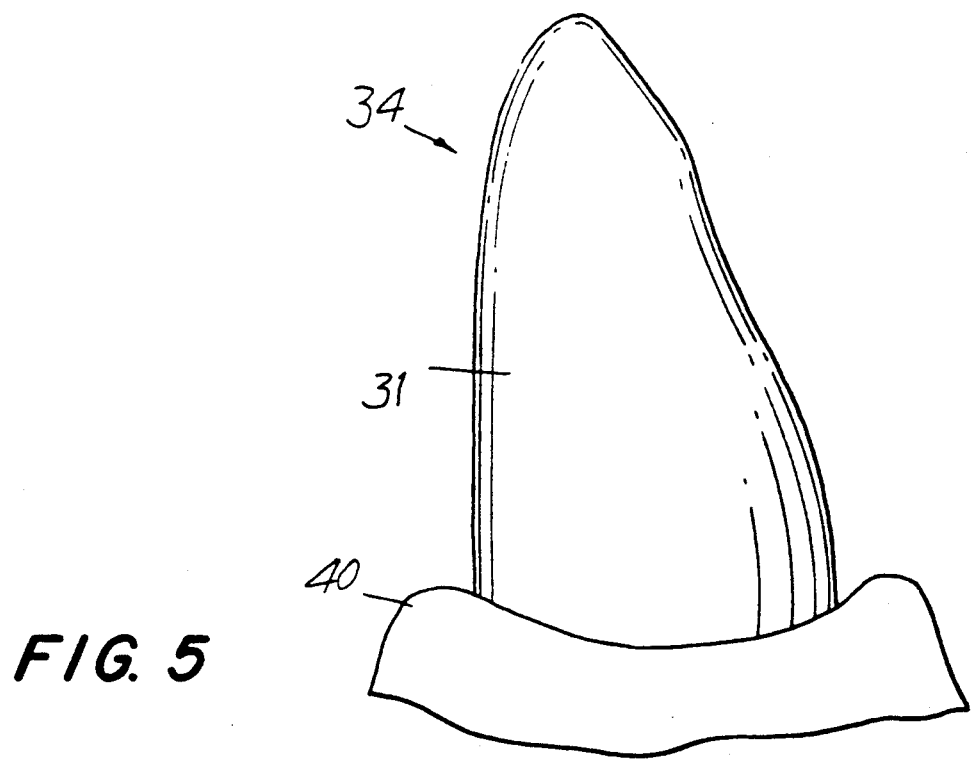
FIG. 5

5,100,322

WATER-COOLED FRICTION CONTOUR CUTTING DENTAL TOOL

CROSS REFERENCE TO RELATED APPLICATION

This is a continuation in part of Application Ser. No. 07/446,756 filed Dec. 6, 1989, now U.S. Pat. No. 5,037,300.

BACKGROUND OF THE INVENTION

1. Field of the Invention

The present invention relates to a tool to be used in dentistry and the use of this tool in new methods for the emplacement of dental prostheses. More particularly, the present invention relates to a rotary cutting tool which is useful for the contouring of a tooth to a uniform, circumferential depth, and, optionally, the undercutting of the tooth surface.

2. State of the Art

It is conventional practice in dentistry to apply a veneer prosthesis to a tooth which has been damaged either as a result of trauma or disease, i.e. caries. Generally, the surface enamel of the tooth is partially removed by grinding to form a relatively even surface, and a dental prosthesis secured to the tooth. Such a prosthesis can be formed extra-orally from a mold taken of the tooth and the surrounding portion of the mouth, which is then adhesively secured to the previously ground down surface; or by applying a moldable composite substance to the contoured tooth substrate, which can be formed in situ on the tooth substrate, and then set and hardened in situ.

Such a veneer is generally not subject to the extreme structural stress to which the facing transverse surfaces of teeth are subject, but rather, is applied to a well-supported vertical, buccal or labial existing surface. The veneer is intended primarily for cosmetic purposes, but also to protect the remaining tooth from further damage caused by chemical or bacterial action. Great care must be taken to insure that the veneer is securely applied to the tooth substrate so as to not only be cosmetically satisfactory, but also insure against displacement during any chewing function.

In teeth which have received more extensive damage, major portions of the tooth's surface may be replaced by a full crown. Normally the tooth is prepared by cutting away the outer surface and contouring the tooth to a desired shape which will support and help retain the crown. A mold is then made of the prepared tooth in order to shape externally, or extra-orally, the portion of the crown which will be in contact with the adjacent teeth. The resulting crown is thereafter mounted and cemented on the prepared tooth. In situ shaping, and curing to hardness, is also possible for full crowns. Various tools have been developed to shape the tooth, such as seen in U.S. Pat. No. 2,250,058 issued Apr. 8, 1940, to Brooks, or U.S. Pat. No. 4,473,354 issued Sept. 25, 1984, to Rigaud, or in British Patent Specification No. 732,124, published on June 22, 1955.

SUMMARY OF THE INVENTION

It is an object of the present invention to provide a new tool which allows a dentist to use improved procedures for the attachment of veneers, jackets or crowns to teeth. This tool and related procedures improves the efficiency of prior art procedures to accomplish similar purposes, and to strengthen the bonding and stability of such veneers, jackets, and crowns (hereinafter collectively referred to as "dental prosthesis") mounted by use of such tool and procedures. It is yet a further object of the present invention to provide a new, improved tool for more efficiently reduced the tooth to a uniform, predetermined depth, for applications of a uniformly thick full crown, which fits against and is compatible with the remaining teeth.

These and other objects are achieved in accordance with the present invention through the employment of the tool of the present invention. The tool has an elongated shank portion, one end of the shank portion being designed to be conventionally secured to a driving member, such as a dentist's drill handpiece, for causing rotation of the tool. The second end of the shank is secured to one end of an elongated cutting tool section; the cutting tool section has a second end, which is open to an interior space extending into the interior of the cutting tool. The cutting tool section has a generally cylindrical shape but can be frustoconical, i.e, expanding its diameter slightly towards its second end, distal from the shank; the cutting tool section end is hollow, at least adjacent such second end. The exterior circumferential surface of the cutting tool section is formed of a hardened, shaped cutting material, or preferably is coated with an abrasive material, such as diamond dust. The second end of the cutting tool section, farthest from the shank, is provided with a transverse, annular end cutting surface, surrounding a central opening into the interior, or hollow, space within the second end of the cutting portion; the transverse end surface is preferably perpendicular to the axis of the cutting tool.

Secured, preferably removably, so as to be substantially centered, within the hollow space is a generally elongated member, which is preferably concentric to, and similarly shaped as, the hollow space, and sized so as to define an annular channel between the outer surface of the elongated member and the interior surface of the cutting tool section defining the hollow space. One end of the elongated member protrudes through the central opening and beyond the annular end cutting surface, so as to limit the cutting depth of the tool into the tooth, both longitudinally and radially.

The protruding end of the elongated member, extending beyond the transverse cutting end surface, preferably is generally cylindrical, and has a smooth rounded surface, most preferably of a relatively soft material, so as not to cut into or damage tooth or gum surfaces. The protruding end is preferably sufficiently smooth, having as low a coefficient of friction as is available, with respect to the exterior surface of a tooth or gum tissue; such low friction is as important as softness for this purpose. Thus, materials useful for forming the protruding end member include such relatively soft metals as aluminum, copper, brass and precious metal alloys (especially as thin veneers over a base metal) such as gold or platinum alloys; solid synthetic polymers, such as polycarbonates; or even ceramic materials, cast and polished to extreme smoothness, regardless of their relative hardness. In addition, a smooth, very thin coating of a low friction material, e.g., a fluorocarbon polymer, such as Teflon, can be applied to the solid substrate of the rounded end.

The elongated portion of the protruding member extending beyond the cutting end surface should be substantially circular in cross-section, as shown by FIG. 2. However, the rounded end need not be a hemisphere, or any lesser spherical surface. Any smooth rounded end surface can provide the desired contact without injury to the gum tissue when contacted.

The extent to which the rounded end of the elongated member protrudes beyond the end cutting surface can be varied, as a means for accurately varying the perpendicular, i.e. axial, distance between the depth limiting surface and the transverse end cutting surface. Similarly, the cross-sectional diameter ("Y") of the elongated protruding portion extending beyond the transverse cutting surface can also be varied, to vary the radial cutting depth. Varying of there dimensions can be accomplished by changing the elongated member, or be, e.g., providing adjustment means to vary the extent to which the member protrudes.

A plurality of transverse longitudinal slots extend through the circumferential cutting surface of the tool, extending to the hollow space. These slots extend transversely to the axis of the cutting tool, preferably at an angle of not more than about 45°. Preferably there are not more than two of these slots, separated by about 180 degrees from each other. If there are more than two such slots, they are preferably to be arranged equidistant about the circumference of the cutting tool section, and preferably extend at supplementary angles to the tool axis.

The tool is preferably hollow along at least a major part of the length of the cutting tool section, to allow for liquid or air cooling of the cutting surface and for ground tooth displacement and removal during cutting. As a further aid in removal of ground material, the hollow shaft has the plurality of slotted openings which allow communication and passage of material between the interior of the hollow shaft and the exterior.

The size and configuration of the enlarged annular ring allows the tool to be used to contour the tooth surface in various ways, thereby improving the methods for permitting securing dental prostheses to existing teeth. When the cutting tool has a frusto-conical shape, it simplifies the creation of an undercut groove at the base of a prepared tooth into which a gasket can be positioned to form a seal with the dental prosthesis; and/or the sculpting of the outer surface of a tooth to prepare it for the application of a prosthesis. Any undercut portion, of course, must be blocked out when forming the mold or the die, when fabricating the crown extra-orally

BRIEF DESCRIPTION OF THE DRAWINGS

Further details of the present invention are shown in the accompanying drawings, by way of a preferred example and not by way of exclusion. Many portions of the invention, or the context thereof, are shown in schematic representation, where greater detail is unnecessary as it is apparent or well known to those skilled in the art. Referring to the accompanying drawings:

FIG. 4 is a cross-section view of the tooth and tool of FIG. 3;

FIG. 4a is a top plan view of a contoured tooth having a uniformly wide flat shoulder;

FIG. 5 is a side view of the tooth of FIG. 3, prior to its being prepared in accordance with the present invention;

DETAILED DESCRIPTION OF THE ILLUSTRATED EMBODIMENTS

Figure 1:
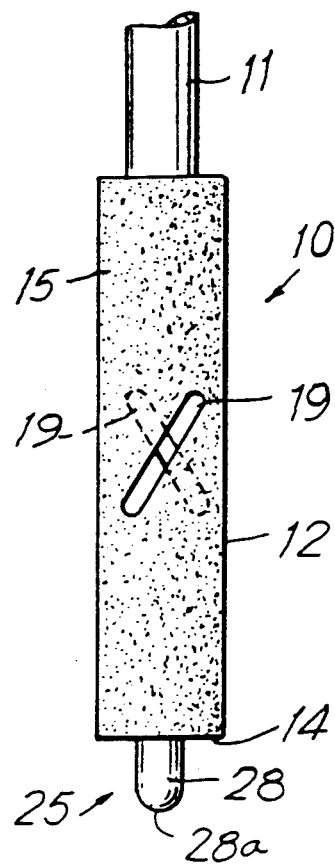
FIG. 1 is a side view of a tool in accordance with the present invention.

The drawings show the dental tool 10 of the present invention. The tool 10 has an elongated shank portion 11 of conventional construction to be secured to a rotational driving means, such as a latch or friction grip type handpiece on a dentist's drill. The remainder of the tool 10 primarily consists of a larger diameter, substantially cylindrical cutting tool section 12, having, preferably, a larger diameter than the shank 11.

The portion of the cutting tool section 12 farthest from the shank 11 has a cavity 18 formed therein, defined by an internal circumferential surface 17. At the end of the cutting tool section 12 farthest from the shank 11, there is an annular transverse surface 14 which surrounds a central opening into the cavity 18. The outer diameter of the annular end surface 14 has the maximum outer diameter of the tool.

The circumferential cutting surface 15 can form an angle of from about 80 degrees to about 90 degrees with the end cutting surface 14, but preferably is perpendicular to the end cutting surface.

The cutting surface of the tool 10 is in the form of an abrasive coating secured to the outer circumferential surface 15, and to the transverse end surface 14. It may be formed by adhering any conventional abrasive coating for dental drill bits and the like, including, e.g., diamond chips.

As seen in FIG. 4, the hollow portion 18 need not extend the entire length of the cutting tool section 12. It is preferred, however, that the hollow passage extends along at least about 50% of the length of the cutting section 12. The hollow space allows passage of a stream of liquid or air for cooling of the drilling operation and/or for ground tooth displacement and removal. The length of the cutting tool section is most preferably at least as long as the height of teeth to be contoured, e.g. about 0.2 inch.

Figure 3:
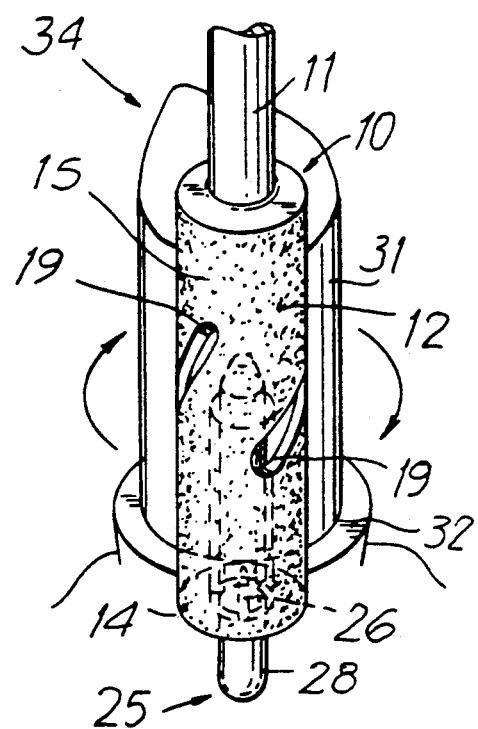
FIG. 3 is a pictorial representation of the tool of FIG. 1 being used to recontour and prepare the core of a tooth to accept a prosthesis.
Figure 2:
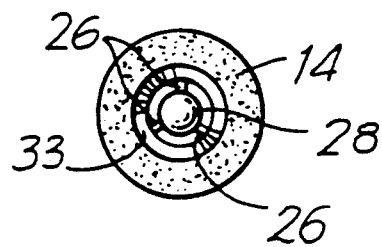
FIG. 2 is a bottom view of the tool of FIG. 1.
Figure 6:
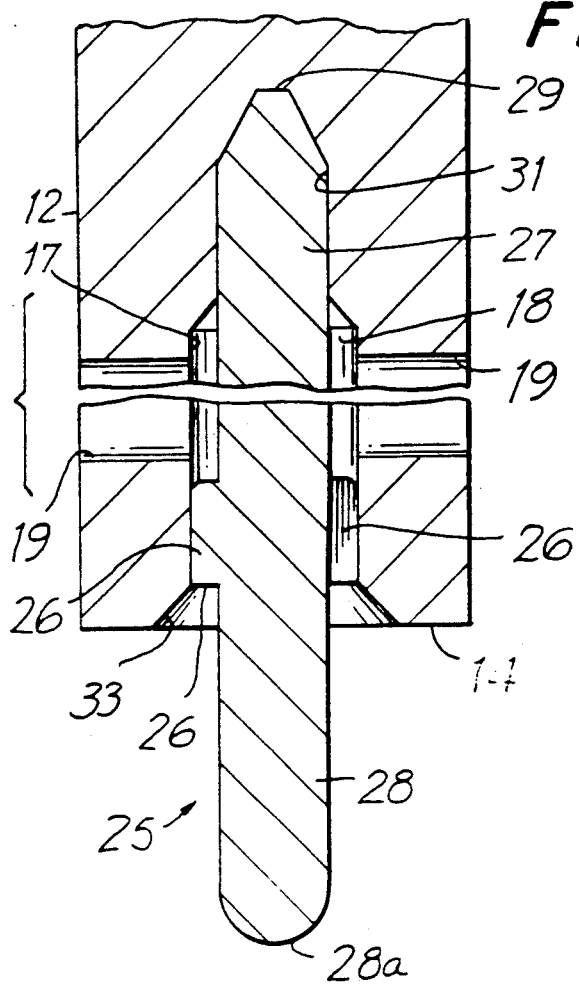
FIG. 6 is an enlarged axial cross sectional view of the lower-cutting portion of the tool of FIG. 1.
Figure 7:
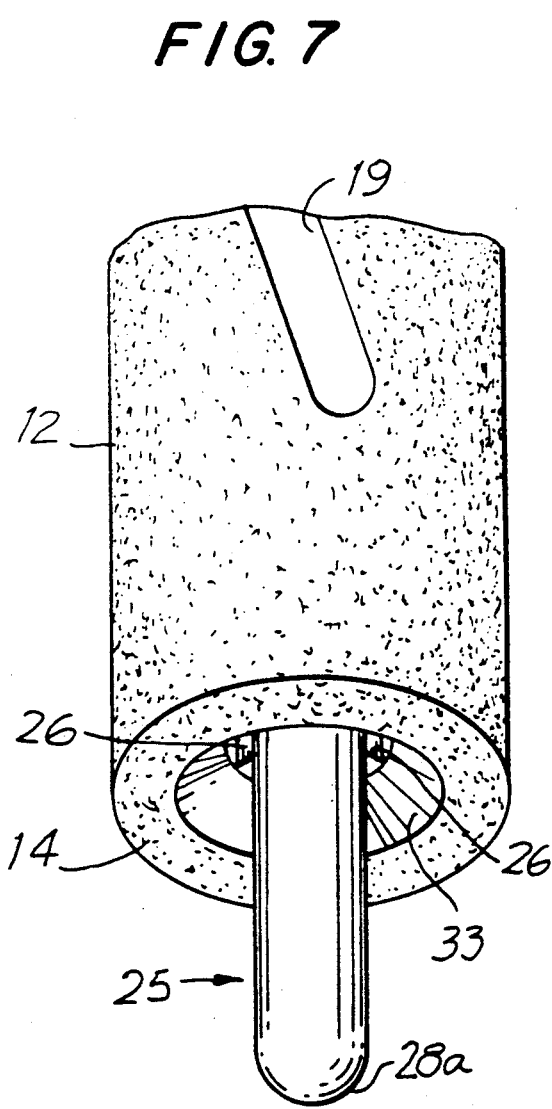
FIG. 7 is an enlarged, broken side elevation view of an insert for mounting into the hollow space within the tool of FIG. 1.

To allow for the passage of ground tooth chips away from the drilling surface, and the entry of cooling water into the opening, the hollow tool section 12 preferably has one or more slot openings 19 communicating through the outer circumference of the tool section 12 with the interior hollow portion 19. As seen in FIGS. 1, 3 and 6, in the preferred embodiment, two or more such openings 19 can be spaced equally around the circumference of the cutting tool section 12. The openings 19 allow communication and passage of material between the interior cavity 18 of the cutting tool section 12 and the exterior space, beyond the outer diameter of the tool section 12, such as cooling water sprayed against the exterior of the cutting tool, which can pass inwardly, and tooth particles, which can pass outwardly. The openings 19 also allow for insertion of a tool (not shown) for removal of any solid particulate material trapped in the hollow portion 18 of tool section 12. The slots preferably extend at an angle of from about 5 to about 15 degrees to the longitudinal axis of the tool, and have a length of at least about 15%, and preferably from about 20% to about 25%, of the length of the cutting tool section 12.

To control the extent of tooth material removal, i.e., the depth of cutting, a generally cylindrical insert, generally indicated by the numeral 25, is removably secured and positioned in cavity 18. One end 27 of the cylindrical insert 25 is secured, as by a friction fit, to the inward most end of the cavity 18. As shown, the external shape and diameter of the upper end 29 of the cylindrical insert 25 is designed to tightly mate with the upper portion 31 of the cavity 18. In the embodiment shown, the cylindrical insert 25 is of substantially constant diameter (except at the very end portions), and the internal diameter of the cavity increases stepwise, towards the transverse cutting end 14.

To simplify insertion and placement of the insert 25, an internal chamfered surface 33 is formed between the cutting end surface 14 and the internal circumferential surface of the cutting tool. In the example shown, the chamfer 33 extends at an angle of about 45° to the end cutting surface 14 and to the axis of the tool, the chamfer also provides for a larger gap between the insert 25 and the end cutting surface 14 than the thickness of the annular channel.

A plurality of vanes 26 are integrally formed, on or secured to, a portion of the cylindrical insert 25 adjacent the cutting end surface 14 to center the cylindrical insert 25 within the cavity 18, without blocking flow through the annular channel formed between the cylindrical insert 25 and the interior cavity surface 17. As shown, there are three equidistantly spaced vanes 26 on the cylindrical insert 25, all located at substantially the same axial position along the cylindrical insert 25. For greater stability, the vanes are located, so as to be placed as closely as practical, immediately adjacent most preferably the chamfer 33, when the insert 25 is in place within the cutting tool.

The distal end of the cylindrical insert 25 extends beyond and through the central opening in the end surface 14, to act as a depth limiting stop for the dental cutting tool of this invention. The distal end is formed with a smooth, rounded surface 28, designed so as to not damage or injure the outer surface of a tooth or of softer gum tissue; the distal end surface 28 can be formed of a relatively softer material than the cutting surface, or formed with an extremely smooth surface, as explained above: a coating, such as Teflon, can be applied to reduce friction; any such coating should be very thin. The distal end surface 28 of the insert 25 is thus effective to limit the radial depth of a cut into the tooth, when the circumferential surface of the protruding tip 28 contacts the side of the tooth, and also limits the longitudinal, or axial, cutting distance by making contact with the patient's gum 40.

The diameter of the major portion of the cylindrical insert 25 can be, e.g., about 0.012 in.; the width of the annular end cutting surface 14 can preferably be about equal to the diameter of the cylindrical insert 25; and the width (radially) of the vanes 26 should be, preferably, at least about 0.04 in., which thus also defines the width of the annular internal passage through the cutting tool section. The distance that the rounded end 28a of the cylindrical insert 25 extends beyond the end cutting surface 14 is variable, and is based upon the particular needs of the dentist in shaping a tooth; the extent of the protrusion of the rounded end 28 can be changed by replacing the insert with a shorter or a longer cylindrical insert 25, or there can be provided means to permit limited longitudinal displacement of the cylindrical insert 25 within the cavity 18. For example, the connection between the insert 25 and the tool 12 can be by a threaded connection at the inner end 29 of the insert 25, with an internal thread within the cavity, at the narrower portion 31, plus a locking means to prevent undesirable movement; this permits adjustment of the insert 25 within the cavity 14. In addition, calibrated indexing marks can be formed either on the outer end 28 of the insert, or on a slot through the outer wall of the tool, aligned with an indicator on the insert 25, visible through the slot.

The size and configuration of the cutting tool surface 15 and the annular end cutting surface 14 allows the drill to be used to contour a tooth's surface in various ways. For example, as is shown in the drawings of FIGS. 3, 4 and 4a, the tool 10 can be used to contour the circumferential tooth surface 31 and to form an upwardly facing shoulder, or ledge, 32, by circumferentially removing a uniform thickness of the enamel surface of the tooth, so that the tooth 34 is prepared to receive a dental prosthesis. The ledge 32 can be slightly undercut, if desired and a gasket can be mounted on the undercut ledge 32, formed after the contouring, to form a seal between the pre-molded dental prosthesis and the prepared tooth 34. This tool permits a single step in the preparation of the tooth for a prosthesis, and eliminates the need for more than one type of tool, in many cases.

I claim:

1. A tool for shaping and undercutting a portion of a tooth, the tool comprising an elongated shank, a first end of the shank being adapted to be secured to a driving means; an elongated, at least partially hollow, cutting tool section, extending from and secured to the second end of the shank, the cutting tool section comprising an external circumferential cutting surface, an interior circumferential surface defining a hollow space, and an external annular, transverse end cutting surface distal from the shank, the end cutting surface surrounding a central opening to the hollow space of the cutting tool section; a generally elongated member, secured so as to be substantially concentric to and held partially within the hollow space, and having a cross section of a dimension such that an annular channel is defined between the elongated member and the interior circumferential surface, one end of the elongated member having a smooth rounded surface and extending through the central opening and beyond the annular cutting surface, so as to limit the cutting depth of the tool, both longitudinally and transversely.

2. The tool of claim 1 wherein each cutting surface comprises an abrasive coating, which acts as a grinding surface.

3. The tool of claim 2 wherein the abrasive coating comprises particulate diamond material.

4. The tool of claim 1 in which the external circumferential cutting surface forms an angle of not greater than about 90 degrees to the annular end cutting surface.

5. The tool of claim 4, in which the external circumferential cutting surface forms an angle of between about 86 and about 90 degrees to the annular end cutting surface.

6. The tool of claim 4 in which the end cutting surface is perpendicular to the axis of the tool.

7. The tool of claim 1 comprising a plurality of slotted openings extending transversely through the circumferential cutting surface, in communication with the hollow space in the cutting tool section.

8. The tool of claim 1 in which the elongated member has a second end secured to the tool within the hollow space.

9. The tool of claim 8 in which the second end of the elongated member has a cross-section size and shape which forms a friction fit with a portion of the interior circumferential surface distal from the transverse end surface.

10. The tool of claim 8 further comprising a plurality of radially extending support members extending between the elongated member and the interior circumferential surface, at an axial location proximal the end cutting surface, intended to stabilize the elongated member to prevent radial displacement.

11. The tool of claim 10 wherein the interior diameter of the annular end cutting surface is greater than the maximum internal diameter of the interior circumferential surface at the axial location of the radially extending support members.

12. The tool of claim 11, comprising an internal chamfer surface extending between the internal circumference of the annular cutting surface and the axial location of the radially extending support members.

13. The tool of claim 1 in which the protruding rounded end surface of the elongated member is formed of a relatively softer material than the cutting surface.

14. The tool of claim 13 wherein the protruding rounded end surface is formed of a material selected from the group consisting of aluminum, copper, brass, and such materials plated with noble metal or a fluorocarbon resin.

15. The tool of claim 1 is removably secured to the cutting tool.

* * * * *